United States Patent [19]

Tenta

[11] 4,265,877

[45] May 5, 1981

[54] COMPOSITION CONTAINING SODIUM FLUORIDE IN A CHEWING GUM BASE

[76] Inventor: Louis T. Tenta, 6007 N. Sheridan Rd., Apt. 24A, Chicago, Ill. 60660

[21] Appl. No.: 123,682

[22] Filed: Feb. 22, 1980

[51] Int. Cl.³ .................. A61K 9/68; A61K 7/18; A61K 33/16

[52] U.S. Cl. ..................... 424/48; 424/52; 424/151; 426/3

[58] Field of Search .................. 424/48–58, 424/151; 426/3–8

[56] References Cited

U.S. PATENT DOCUMENTS

| | | | |
|---|---|---|---|
| 50,578 | 10/1863 | Hamilton | 424/49 |
| 801,317 | 10/1905 | James | 424/49 |
| 2,627,493 | 2/1953 | Merckel et al. | 424/52 X |
| 2,700,012 | 1/1955 | Merckel et al. | 424/52 X |

*Primary Examiner*—Shep K. Rose
*Attorney, Agent, or Firm*—Hill, Van Santen, Steadman, Chiara & Simpson

[57] ABSTRACT

A composition for enhanced oral absorption of fluoride ions which includes a chewing gum base, and a mixture of sodium fluoride and calcium carbonate in the form of oyster shell distributed within the base. The composition is suitable for use as a dietary supplement, as an agent for reducing the possibility of dental caries, and for the treatment of bone metabolism conditions.

5 Claims, No Drawings

COMPOSITION CONTAINING SODIUM FLUORIDE IN A CHEWING GUM BASE

BACKGROUND OF THE INVENTION

1. Field of the Invention

This invention is in the field of compositions for introducing controlled amounts of fluoride ions into the circulatory system. The composition of the present invention is a chewing gum containing sodium fluoride and calcium carbonate in the form of oyster shell and provides a novel route for the oral administration of fluoride ions by means of the orobuccal phase.

2. Description of the Prior Art

Extensive studies on the part of the U.S. Public Health Service several decades ago established that the fluoridation of water could be employed as a practical measure to reduce the incidence of tooth decay. It has now been definitely established on the basis of large scale studies in a number of communities that the fluoridation of water to a concentration of 1.0 ppm is a safe and practical public health measure which results in a 50 to 66% reduction in the incidence of dental caries in permanent teeth. There is also evidence to show that the topical application of 2% sodium fluoride to the teeth of children may reduce the incidence of caries as much as 40%.

More recently, it has been demonstrated in a 15-year study that the administration of sodium fluoride in relatively small amounts during pregnancy resulted in an almost complete elimination of dental caries in the subsequently born children. (Glenn, *Journal of Dentistry for Children*, January, 1980.)

There has also been a disclosure of incorporating sodium fluoride into a chewing gum in the patent art, as evidenced by U.S. Pat. Nos. 2,627,493 and 2,700,012 of Merckel et al. The specifications of the two patents are the same, both dealing with the inclusion of sodium fluoride into chewing gum bases. The problem sought to be overcome by the Merckel et al patents was the interaction of sodium fluoride with calcium compounds, particularly calcium carbonate whether present as an ingredient in the chicle or as a filler. In the '493 patent this was accomplished by dissolving out the calcium compound by means of a strong acid and then washing out the resulting salt. In the '012 patent, the calcium was more or less deactivated by reacting the same with an oxalate, phosphate, or the like which, according to the theory expressed in the specification, immobilized the calcium, preventing its reaction with the sodium fluoride.

The absorption of fluoride ions from the gastrointestinal tract varies considerably. A number of fluoride preparations are available in liquid, gel, compressed tablets, and gelatin capsule encased powders. The testing of such preparations was reported by Deka et al in "The Laryngoscope", Volume 88 (1978). This article reported on the gastric intestinal absorption of five different preparations of sodium fluoride, measured by 10-hour urinary excretion. It was found that the best absorption was by nonenteric coated sodium fluoride. All three enteric coated preparations showed poorer absorption, with marked individual variations. The combination of sodium fluoride and calcium carbonate present in oyster shell showed better absorption than the enteric coated tablets and only slightly less than sodium fluoride alone.

SUMMARY OF THE INVENTION

The present invention provides an improved composition for oral administration of fluorides in conjunction with a chewing gum base. Specifically, the present invention makes use of a combination of sodium fluoride and calcium carbonate derived from oyster shell in a chewing gum base as a longer-lasting, faster-acting agent for introducing fluoride ions into the metabolism of bone and dentition. A stick of the improved chewing gum may be considered a unit dosage form of the composition, and typically contains, for every 3 gram stick, about 1.1 to 8.3 mg of sodium fluoride, and 54 to 364 mg of oyster shell. The composition may also include a sweetening agent, either natural or synthetic.

DESCRIPTION OF THE PREFERRED EMBODIMENTS

The composition of the present invention has been found to eliminate many of the defects previously associated with the administration of fluoride orally.

Currently available oral preparations including fluorides, as previously observed, exhibit varying absorption characteristics from the gastrointestinal tract. This absorption is influenced by the solubility quotient of the fluoride compound which is employed and may be influenced by the coincidental administration of other elements such as aluminum, magnesium or calcium which may combine with the fluoride ion and form relatively less soluble and consequently less absorbable compounds.

In addition, certain conditions such as the demineralization of bone that occurs with osteoporosis call for the coincidental oral administration of calcium and magnesium ions with fluoride ions as part of the therapeutic plan, thereby enhancing the probability of forming relatively less soluble fluoride compounds.

Certain other conditions may exist which further affect the gastrointestinal phase of fluoride absorption, namely:

gastrointestinal malabsorption syndromes
swallowing disorders
gastrostomy patients
patients with intestinal shunt procedures
patients with bowel resections
patients receiving calcium or aluminum or magnesium based antacids, cathartics or food supplements.

The improved results of the present invention were confirmed by a fluoride absorption and excretion study showing that heretofore unanticipated and unrecognized orobuccal phase of fluoride absorption occurs when the combination of sodium fluoride and oyster shell calcium carbonate is incorporated into a chewing gum base. This orobuccal phase provides a novel route for the oral administration of fluoride which is effective in the management of those patients in need of fluoride supplementation who may also be in the aforementioned categories by eliminating the potential of forming less soluble fluoride compounds or minimizing the consequences of altered absorption characteristics of the gut as a result of disease or surgery.

The oyster shell which is employed as the source of calcium carbonate (in addition to any calcium carbonate normally occurring in the gum base) consists of about 97% calcium carbonate and 3% of a mixture of trace elements such as magnesium, silicon, manganese, iron, aluminum, copper, sodium, strontium, potassium, and zinc. It is believed these trace elements substantially enhance the absorption charcteristics of the new composition.

The most common chewing gum base is chicle. In addition, various types of natural or synthetic gums can be used as the carrier material for the sodium fluoride-oyster shell combination. Suitable gum bases include gutta percha, jelutong, balata, namaquland rubber, almeidana gum, abba rubber, and the various gutta rubbers. The gum bases may also be resins such as cumarone resins, copal gum, kauri gum, dammar gum, sweet bay gum, spruce gum, and balsams. The chewing gum base may also consist of synthetic elastomers such as polyisobutylene, polyisoprene, and copolymers of butadiene and styrene. Hydrogenated or partially hydrogenated vegetable oils such as soy bean oil, cottonseed oil, corn oil, peanut oil, and palm or animal fats such as tallow and lard can also be used. Paraffin, beeswax, petroleum wax, polyethylenes, and polyvinyl polymers are other examples of materials which can be used.

Each 3 gram stick of gum may contain from about 1.1 to 8.3 mg of sodium fluoride, and 54 to 364 mg of oyster shell. Optimum values are 2.34 mg of sodium fluoride and 103.92 mg of oyster shell. Generally speaking, there should be about 40 to 50 times as much oyster shell present as there is sodium fluoride.

The composition may also include a natural or synthetic sweetening agent in an amount of about 10 to 80% by weight of the entire composition. Such sweeteners include dextrose, fructose, sorbital, xylitol, mannitol, saccharin, or similar compounds.

Combining the sodium fluoride with calcium carbonate in the form of oyster shell into a chewing gum base permits a slower descent of these agents from the oral cavity into the stomach in contrast to the direct act of swallowing a capsule or liquid as a bolus containing these compounds. The undesirable rapid urinary excretion of fluoride associated with the bolus effect is eliminated, and a slower, more sustained absorption of fluoride is obtained.

It was found in the aforementioned study that subjects chewing the improved gum of the present invention demonstrated sharp rises in urinary fluoride levels immediately after the chewing of the gum, indicating a rapid assimilation of fluoride into the circulatory system. It appears, therefore, that the fluoride incorporated into the chewing gum permits the oral or buccal absorption of the ion. After the initial fast rise, the urinary fluoride levels varied in each subject. This divergence is reconciled by the suggestion that after the initial rise of fluoride level, each subject drank about 300 ml of distilled water, thereby washing any residual fluoride containing saliva from the mouth into the gastrointestinal tract, from which the variation and absorption of fluoride ions is well known.

The compositions of the present invention thus provide a safe and effective means for the oral administration of fluoride on a sustained basis.

It should be evident that various modifications can be made to the described embodiments without departing from the scope of the present invention.

I claim as my invention:

1. A composition for enhanced oral absorption of fluoride ions comprising a chewing gum base, and a mixture of sodium fluoride and calcium carbonate in the form of oyster shell distributed within said base, said oyster shell being present in an amount sufficient to enhance the absorption of fluoride ions from the gastrointestinal tract including the oral and buccal mucosa.

2. A composition according to claim 1 in unit dosage form, each unit dosage including from 1.1 to 8.3 mg of sodium fluoride.

3. A composition according to claim 2 which contains from 54 to 364 mg of oyster shell.

4. A composition according to claim 3 in which said unit dosage form is a stick of gum weighing approximately 3 grams.

5. A composition according to claim 1 which also includes a sweetening agent.

* * * * *